United States Patent [19]

Hjelmeland

[11] 4,372,888

[45] Feb. 8, 1983

[54] NONDENATURING ZWITTERIONIC DETERGENTS

[75] Inventor: Leonard M. Hjelmeland, Bethesda, Md.

[73] Assignee: The United States of America as represented by the Secretary of the Department of Health & Human Services, Washington, D.C.

[21] Appl. No.: 294,203

[22] Filed: Aug. 19, 1981

Related U.S. Application Data

[63] Continuation-in-part of Ser. No. 181,465, Aug. 26, 1980, abandoned.

[51] Int. Cl.³ .............................................. C07J 9/00
[52] U.S. Cl. .................................. 260/397.1; 564/193
[58] Field of Search .............................. 260/397.1, 557; 252/545, 547

[56] References Cited

U.S. PATENT DOCUMENTS 3,910,888 10/1975 Widauer et al. ................. 260/397.1
4,104,285 8/1978 Torres et al. .................... 260/397.1
4,264,514 4/1981 Hixson, Jr. et al. ............. 260/397.1

FOREIGN PATENT DOCUMENTS 1037645 8/1966 United Kingdom ............ 260/397.1

*Primary Examiner*—Elbert L. Roberts
*Attorney, Agent, or Firm*—John S. Roberts, Jr.

[57] ABSTRACT

A nondenaturing zwitterionic detergent for proteins which, for example, consists of an effective amount of 3-[(3-chloamidopropyl)dimethylammonio]-1-propanesulfonate (CHAPS). This detergent is of extreme interest in the biological study of proteins due to its nondenaturing characteristic. Other examples of the group may be prepared from different alicyclic compounds, for example, utilizing cholic acid and in others deoxycholic acid and dehydroabietic acid. A process for the preparation of these compounds starts with cholic or the equivalent and from this is prepared the triethylammonium salt in tetrahydrofuran (THF). After the salt is completely dissolved in THF, ethyl chloroformate is added and the flask cooled to 0° C. Then the mixed anhydride which forms is reacted with dimethylaminopropylamine to form the dimethylaminopropyl derivative of a carboxylic acid amide. Finally, the tertiary amine group is reacted with propanesultone to give the sulfobetaine product.

An improved procedure for preparation of these compounds and especially for the last step (as for CHAPSO) to react the N-(3-dimethylaminopropyl)cholamide with sodium-1-chloro-2-hydroxy-3-propanesulfonate.

6 Claims, 2 Drawing Figures

NONDENATURING ZWITTERIONIC DETERGENTS

This application is a continuation-in-part of pending Ser. No. 181,465 filed Aug. 26, 1980. now abandoned.

This invention relates to a nondenaturing zwitterionic detergent for proteins which, for example, consists of an effective amount of 3-[(3-chloamidopropyl)-dimethylammonio]-1-propanesulfonate (CHAPS). This detergent is of extreme interest in the biological study of proteins due to its nondenaturing characteristic. Other examples of the group may be prepared from different alicyclic compounds, for example, utilizing cholic acid and in others deoxycholic acid and dehydroabietic acid. A process for the preparation of these compounds starts with cholic or the equivalent and from this is prepared the triethylammonium salt in tetrahydrofuran (THF). After the salt is completely dissolved in THF, ethyl chloroformate is added and the flask cooled to 0° C. Then the mixed anhydride which forms is reacted with dimethylaminopropylamine to form the dimethylaminopropyl derivative of a carboxylic acid amide. Finally, the tertiary amine group is reacted with propanesultone to give the sulfobetaine product.

This application is an improved procedure for preparation of these compounds and especially for the last step as for CHAPSO to react the N-(3-dimethylaminopropyl)cholamide with sodium 1-chloro-2-hydroxy-3-propanesulfonate.

PRIOR ART STATEMENT

W. F. Simonds, et al, "Solubilization of Active Opiate Receptors," *Proc. Natl. Acad. Sci., USA*, Vol. 77, No. 8, pp. 4623–4627, August 1980.

N. Parris, et al, *J. Amer. Oil Chem. Soc.*, 53, 60–63 (1976).

U.S. Pat. No. 4,104,285 Gallo-Torres et al—taurine and glycine derivatives, which compounds lack the ammonio fraction present in the instant compounds.

U.S. Pat. No. 4,264,514 Hixson et al—measuring the level of conjugated bile acids.

Gonenne et al, "Solubilization of Membrane Proteins by Sulfobetaines, Novel Zwitterionic Surfactants," *Analytical Biochemistry*, 87:28–38 (1978).

Hjelmeland et al, "Electrofocusing of Integral Membrane Proteins in Mixtures of Zwitterionic and Nonionic Detergents," *Analytical Biochemistry*, 95:201–208 (1979).

Parris et al, "Soap-Based Detergent Formulations: XVIII. Effect of Structure Variations on Surface-Active Properties of Sulfur Containing Amphoteric Surfactants," *J. Amer. Oil Chem. Soc.*, 53:97–100 (1976).

Parris et al, "Soap Based Detergent Formulation: XXIV. Sulfobetaine Derivatives of Fatty Amides," *J. Amer. Oil Chem. Soc.*, 54:294–296 (1977).

Parris et al, "Soap Based Detergent Formulations. V. Amphoteric Lime Soap Dispersing Agents," *J. Amer. Oil Chem. Soc.*, 50:509–512 (1973).

Herrmann, "Micellar Properties of Some Zwitterionic Surfactants," *J. Colloid Interface Sci.*, 22:352–359 (1966).

Parris et al, "Determination of Sulfobetaine Amphoteric Surfactants by Reverse Phase High Performance Liquid Chromatography," *Anal. Chem.*, 49:2228–2231 (1977).

Konig, *Z. Anal. Chem.*, 259:191–194 (1972).

British Pat. No. 1,037,645.

DEFINITION

In this specification the following definition from Condensed Chemical Dictionary, 9, page 107, is given. Bile acid and salt are defined as an acid and acid salt found in bile (the secretion of liver); bile acids are steroids having a hydroxy group and a 5-carbon atom side chain terminating in a carboxyl group; cholic acid is mentioned as the most abundant bile acid in human bile.

INTRODUCTION

One of the more important aspects of the purification of membrane proteins is the choice of a suitable detergent. This choice is usually based on the ability to preserve an anzymatic activity or some other native property. In this aspect, non-ionic detergents such as Triton X-100 (octylphenoxy polyethoxy ethanol; Rohm and Haas) and Lubrol PX (polyethoxy lauryl ether, ICI), and the bile salts are the reagents of choice. Two additional considerations must also be made. The first relates to the artificial aggregation of proteins while in the presence of detergents to form nonspecific protein complexes which have no biological relevance. A useful detergent should be capable of breaking such interactions to give maximally disaggregated species in solution. Nonionics are generally less efficient in this respect than are ionic detergents or bile salt anions. The second consideration is the extent to which the detergent affects the charge properties of solubilized proteins. Anionic detergents, for example, add substantial amounts of negative charge which may completely overshadow the charge properties of the native protein. This type of charge alteration profoundly affects the utility of conventional techniques such as ion exchange chromatography and isoelectric focusing which depend primarily on charge properties to effect protein separations.

A survey of existing detergents demonstrates that no single compound which is presently available is adequately nondenaturing, disaggregating, and at the same time electrically neutral. The bile salts are both nondenaturing and effective in disaggregating protein but lack the charge neutrality necessary for compatibility with charge fractionation techniques. In contrast, Triton X-100 and other polyethoxy-type nonionics are electrically neutral and nondenaturing but appear not to be efficient at breaking protein-protein interactions. N-alkyl sulfobetaines are neutral and efficient at disaggregating protein but are unfortunately strongly denaturing. One possibility of a detergent useful in the purification of membrane proteins is a combination of a bile salt hydrophobic group and a sulfobetaine type polar group. This invention describes the synthesis and properties of a sulfobetaine derivative of cholic acid and evaluates its potential utility in membrane protein purification.

C57BL/6 mouse liver microsomes were prepared by differential centrifugation of tissue homogenized in a 150 mM KCl, 10 mM EDTA buffer at pH 7.25, 4° C. For solubilization experiments, the appropriate amount of protein was diluted to give solubilization media with the stated protein and detergent concentrations, and final concentrations of 20% (v/v) glycerol and 0.1 M K phosphate, pH 7.25. Aliquots of 5 ml were incubated for 30 min at 25° C., and then centrifuged at 105,000xg, 25° C. for 2 hr.

The left panel shows the amount of protein solubilized at various concentrations of CHAPS, expressed as a percentage of the amount of protein which could be recovered in the pellet in the absence of detergent. Protein was measured in both the pellet and the supernatant. The right panel shows the amount of cytochrome P-450 remaining in the supernatant at various detergent combinations. These amounts are expressed as percentages of the total P-450 content of the intact microsomes. P-450 was measured as the absorbance at 450 nm minus 490 nm in the reduced vs. reduced+carbon monoxide difference spectrum.

Figure 1:
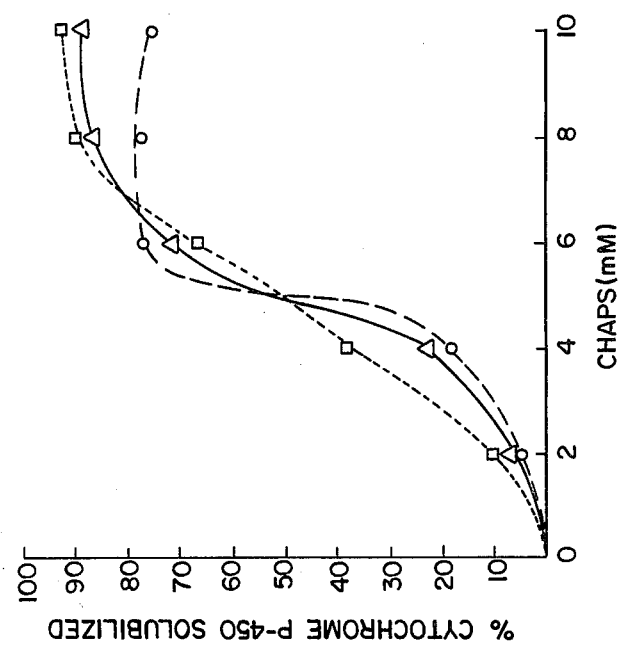
FIG. 1 presents data on the effectiveness of CHAPS in solubilizing mouse liver microsomes and shows that it is nondenaturing with respect to cytochrome P-450 at concentrations up to 10 mM. The left hand panel indicates that CHAPS is capable of solubilizing about 70% of the protein of mouse liver microsomes which can be repelleted in the absence of detergent. Data are given at total protein concentrations of 1, 3, and 5 mg/ml. The sharp break in the three curves between 4 and 6 mM indicates that the critical micille concentration of CHAPS is possibly in this region. The right hand panel of the figure gives the percentage of the total cytochrome P-450 found in the supernatant at each of the same protein and CHAPS concentrations. The higher protein concentrations yield recoveries of soluble and nondenaturated cytochrome P-450 in excess of 90%.
Figure 1:
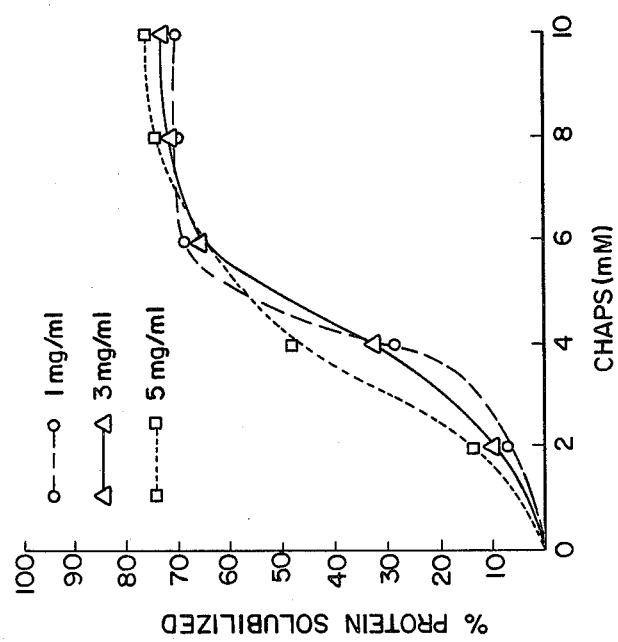

FIG. 1 shows as a dosage an optimum range for solubilizing proteins by CHAPS here given as about 5 mM to 10 mM which gives 50-90% protein solubilization which is non-denaturing. This is a preferred range.

Figure 2:
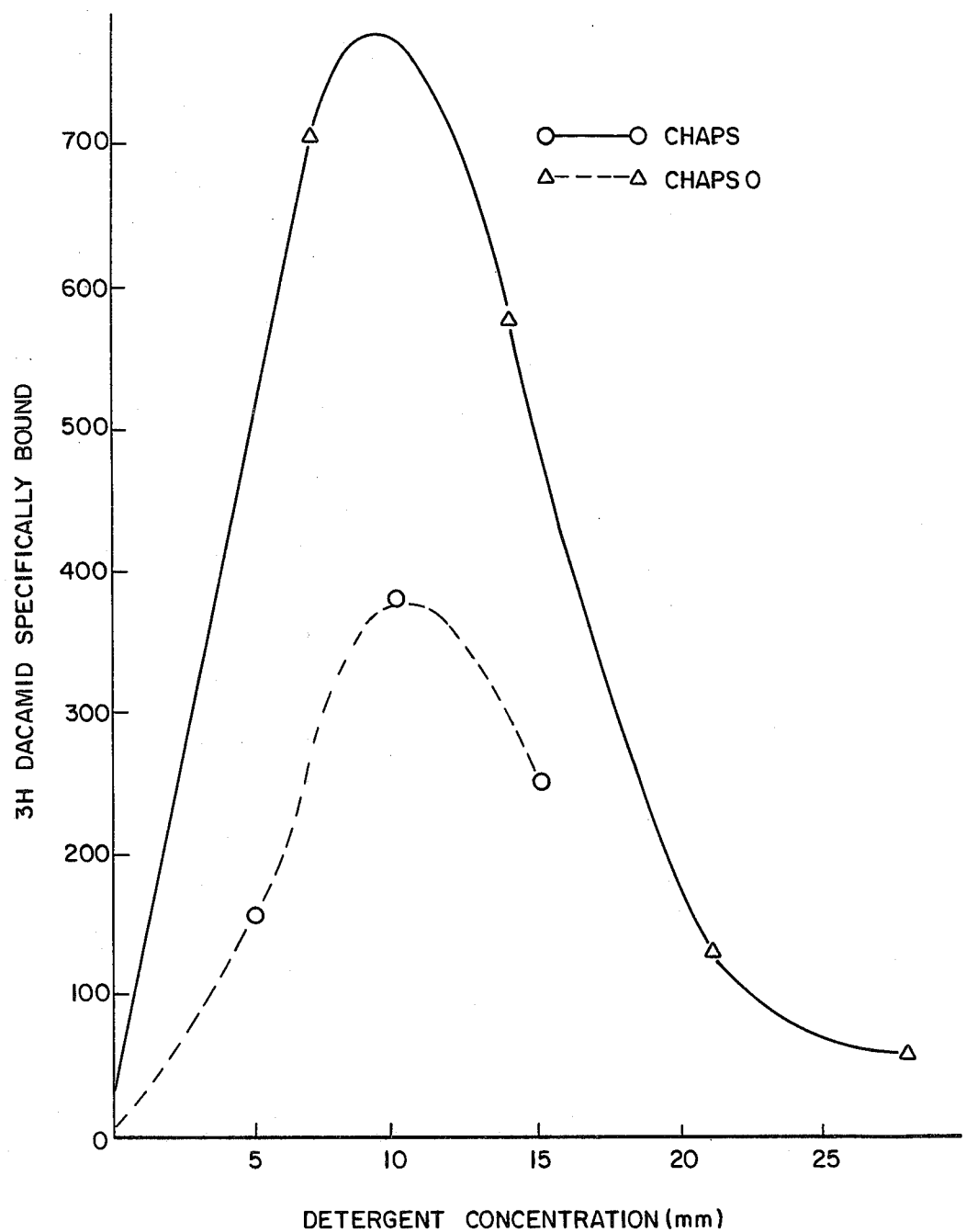

FIG. 2 shows an evaluation of 3-[(3-cholamidopropyl)dimethylammonio]-2-hydroxy-1-propanesulfonate with a 2:1 advantage over CHAPS in solubilizing active opiate receptors.

SOLUBILIZING PROTEIN WITH CHAPS

As a new detergent to be used in the solubilization of membranes, CHAPS combines the useful features of both the bile salts and the n-alkyl sulfobetaines. Like the sulfobetaines, CHAPS proves to be better at solubilizing protein than structurally related carboxylic acid anions. Although it is difficult to compare solubilization results from different tissues under different experimental conditions, studies of the efficiency of solubilization by Na cholate suggest that CHAPS is a substantially better detergent. The data presented here were obtained with microsomes which were treated with 10 mM EDTA and 150 mM KCl to remove extrinsic proteins, which account for perhaps 30% of the most easily solubilized protein in these membranes. By this criterion CHAPS behaves more like Na deoxycholate in its ability to solubilize total protein, although it is structurally more related to Na cholate. CHAPS is, however, much more effective at breaking protein-protein interactions than either Na cholate or Triton X-100. Cytochrome P-450 is normally highly aggregated in solutions containing either of these detergents, but CHAPS disaggregates P-450 to its monomeric form.

The increased capacity of CHAPS to solubilize protein and disaggregate complexes is not gained at the expense of increased denaturing properties. CHAPS is nondenaturing with respect to P-450 under the conditions employed in this invention. This is in contrast to Na deoxycholate, which denatures P-450 under similar conditions. A recent study of the opiate receptor found CHAPS to be the only detergent capable of solubilizing the receptor in a state exhibiting reversible binding of opioids. These are indirect measures of the physical interactions of CHAPS with these proteins and the term "denaturing" is used in its loosest sense.

The most important but less obvious advantage of CHAPS as a detergent for solubilizing membranes is its compatibility with charge fractionation techniques. Sulfobetaines, while being zwitterionic, behave essentially as nonionic compounds. Specifically, they possess no net charge at any pH between 2 and 12, they exhibit no conductivity or electrophoretic mobility, and do not bind to ion exchange resins. This gives sulfobetaine-type detergents a tremendous advantage in both ion exchange chromatography and isoelectric focusing. The utility of n-alkyl sulfobetaines in isoelectric focusing has been demonstrated and preliminary experiments with CHAPS indicate no interference with the formation or stability of pH gradients in this technique.

GENERALIZED PROCEDURE

Below is a step-by-step outline of the synthesis described in this invention.

Step 1. The triethylammonium salt of cholic acid is formed in THF.

Step 2. After the salt is completely dissolved in THF, ethyl chloroformate is added and the flask is cooled to 0° C. At this point, a precipitate is formed which is triethylamine hydrochloride. This is filtered away from the mixed anhydride.

Step 3. The mixed anhydride then reacts with the dimethylaminopropylamine to form a dimethylaminopropyl derivative of a carboxylic acid amide, ethanol, and carbon dioxide as a gas.

Step 4. In the final step, the tertiary amine group is reacted with propane sultone to give the sulfobetaine.

Step 4a. More preferably, in the final step the tertiary amine group is reacted with sodium 1-chloro-propanesulfonate to give the final product. Confer FIG. 2.

Step 1

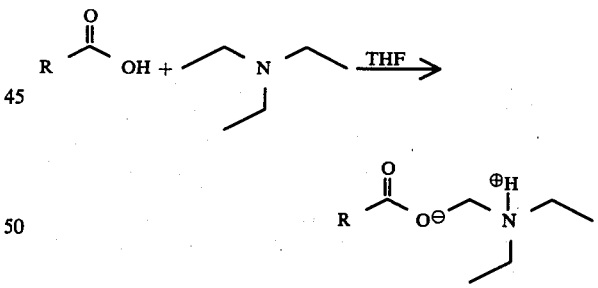

Step 2

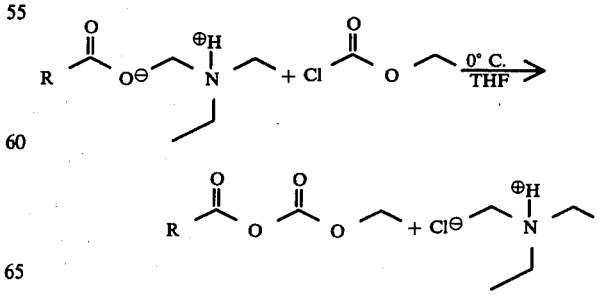

Step 3

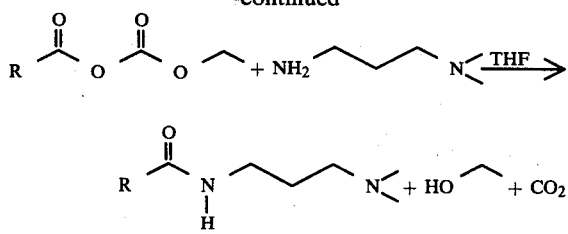

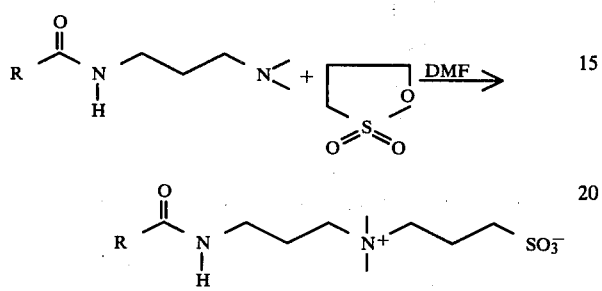

Step 4

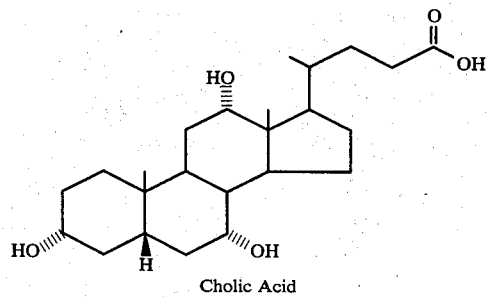

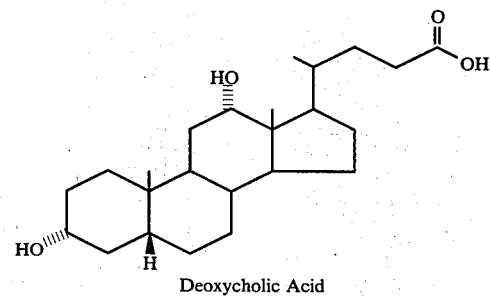

The three important synthetic elements in the final molecule are:
1. The starting carboxylic acid
2. The polyamine used to generate the functionalized amide
3. The alkylating agent used to quaternize the tertiary amine and give the final product.

The carboxylic acids may be:

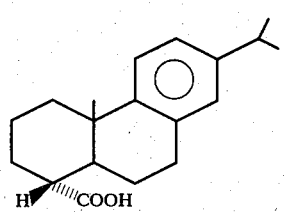

Cholic Acid

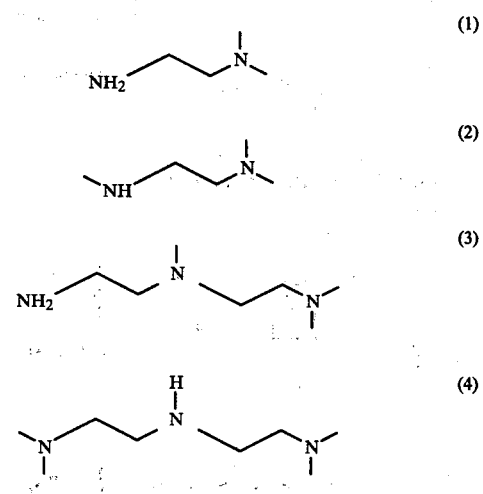

Deoxycholic Acid or

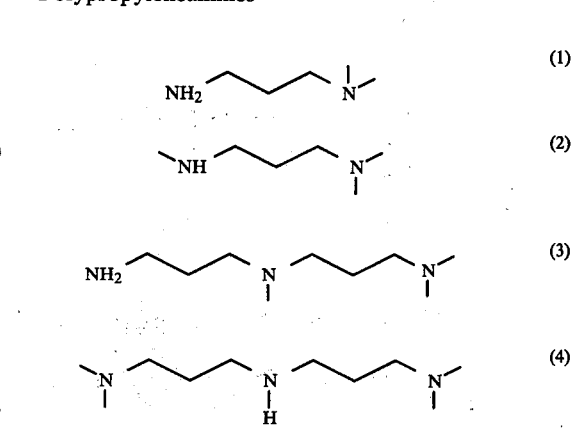

Dehydroabietic Acid

The dehydroabietic acid is important since it represents the most abundant naturally occurring group organic acids, the rosin acids which are refined from wood rosin and tall oil and have wide industrial uses, among them, the synthesis of surfactants.

The polyamines may be:
Polyethyleneamines

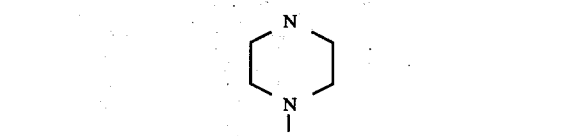

or
Polypropyleneamines

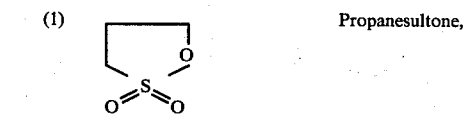

Others—such as N-methyl piperazine

The alkylating agents may be:

(1) Propanesultone,

-continued (2) 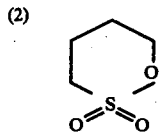 Butanesultone, (3) 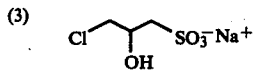 Sodium 3-Cl, 2-OH—Propanesulfonate, (4) 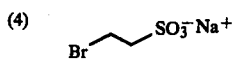 Sodium 2-Br Ethanesulfonate, or (5) 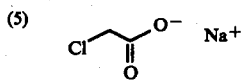 Sodium chloroacetate.

Specific operative compounds are:

(1) 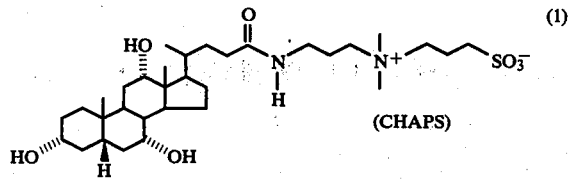 (CHAPS)

(2) 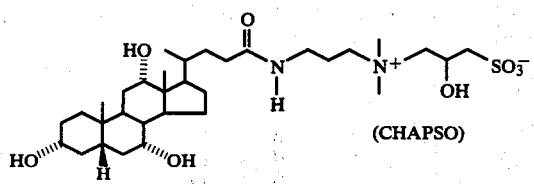 (CHAPSO)

(3) 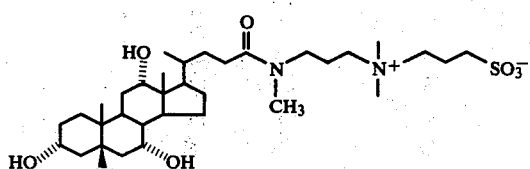

(4) 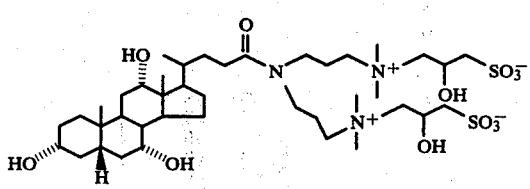

(5) 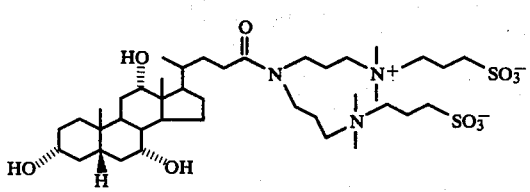

(6) 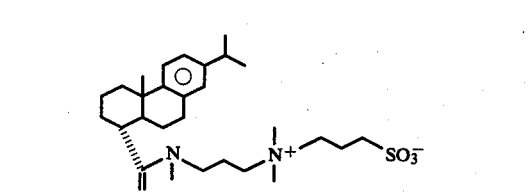

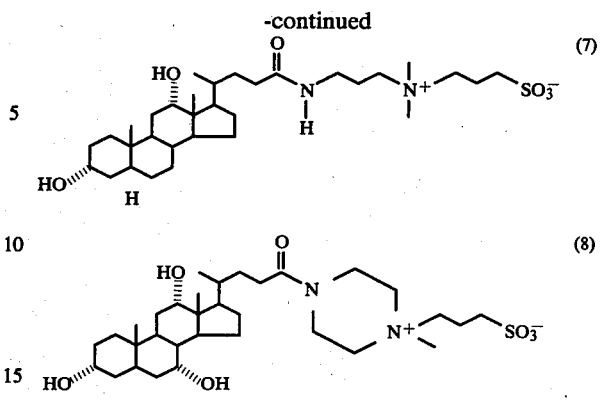

EXAMPLE 1

Synthesis of 3-[(3-cholamidopropyl)dimethylammonio]-1-propanesulfonate

A solution of 40.86 g (0.1 mole) of cholic acid in 500 ml of anhydrous THF was prepared in a 1-liter round bottom flask equipped with a drying tube. To this solution was added 13.95 ml (0.1 mole) of anhydrous triethylamine. The flask was gently swirled, 9.56 ml (0.1 mole) of ethyl chloroformate was added, and the flask was immediately placed in an ice bath for 20 minutes. A voluminous white precipitate was visible at this point.

To a one-liter side arm flask was added 12.54 ml (0.1 mole) of 3-dimethylaminopropylamine and 10 ml of anhydrous THF. The flask was equipped with a 9 cm Buchner funnel and a number 1 Whatman filter circle. The contents of the one-liter flask were then filtered into the side arm flask. Evolution of carbon dioxide was visible as the filtrate mixed in the side arm flask. The round bottom flask was rinsed with an additional 20 ml of THF which was subsequently used to wash the filter cake.

The filtrate was then transferred to a one-liter round bottom flask and the THF removed by distillation at reduced pressure on a rotary evaporator. The residue was taken up in 500 ml of dichloromethane and transferred to a 2-liter separatory funnel. The organic phase was extracted thoroughly with 200 ml of 3 M sodium hydroxide and 15 minutes were allowed for complete phase separation. Small amounts of ethanol (10 ml or less) were used to break any remaining emulsions. The dichloromethane (bottom phase) was drawn off and dried for 30 min. over 50 g of magnesium sulfate. The dried dichloromethane solution was decanted into a 1-liter round bottom flask. The magnesium sulfate was rinsed with an additional 20 ml of dichloromethane, which was then added to the round bottom flask, and all solvent was subsequently removed at reduced pressure in a rotary evaporator. Excess water was then removed by repeatedly adding 50 ml of a 2:1 mixture of toluene and absolute ethanol to the round bottom flask followed by distillation in the rotary evaporator, until no cloudiness was observed in the distilled solvent. Removal of all solvents left N-(3-dimethylaminopropyl) cholamide as a gummy white solid at room temperature.

The gummy white residue from the previous step was taken up in 500 ml of anhydrous DMF and transferred to a 1-liter Erlenmeyer flask equipped with a ground glass joint and stopper. To this solution was added 12.25 g (0.1 mole) of propanesultone and the flask was stoppered and incubated in a water bath at 60° C. for 2 hr. The solution was then cooled to room temperature in an ice bath and 500 ml of absolute methanol were added. The bulky precipitate was broken up, collected on a Buchner funnel by vacuum filtration and the filter cake washed with an additional 200 ml of absolute methanol. The crude product was subsequently triturated in 500 ml of boiling acetone and again collected by vacuum filtration. Thorough drying at room temperature yielded 45 to 50 g of 3-[(3-cholamidopropyl)dimethylammonio]-1-propanesulfonate (CHAPS) (75–80% theoretical).

The crude material was judged to be better than 95% pure by thin layer chromatography on silica gel G in a 95% methanol 5% ammonium hydroxide solvent system. The product appeared as a spot with an $R_f$ of 0.32 which was visualized with iodine, phosphomolybdate, or ninhydrin. The tertiary amine precursor appeared as a spot with $R_f=0.4$.

Analytically pure material was obtained by repeated crystallization at 0° C. from absolute methanol, followed by drying under high vacuum at room temperature to a constant weight. The calculated analysis for $C_{32}H_{58}N_2S_1O_7$ after correction for 4.26% water determined by Karl Fischer analysis was: C 59.85%, H 9.58%, N 4.36, S 4.99; found: C 59.85%, H 9.19%, N 4.24%, S 5.06%.

EXAMPLE 2

Synthesis of 3-[(3-cholamidopropyl)dimethylammonio]-2-hydroxy-1-propanesulfonate (see FIG. 2)

N-(3-dimethylaminopropyl)cholamide was prepared as described in the parent patent appliation, Ser. No. 181,465). Sodium 1-chloro-2-hydroxy-3-propanesulfonate was prepared according to the method described by Parris et al, *J. Amer. Oil Chem. Soc.*, 53, 60–63 (1976).

To a solution of 0.1 mole (49.3 g) of N-(3-dimethylaminopropyl)cholamide in 300 ml of 40% aqueous methanol was added 0.1 mole (15.15 g) of sodium 1-chloro-2-hydroxy-3-propanesulfonate. The mixture was refluxed with stirring for 3 hours, after which the solution was allowed to cool to room temperature and 100 g of RG-501 X8 mixed bed ion-exchange resin (Bio Rad) were added. The suspension of ion-exchange resin was gently stirred until the pH of the supernatant was approximately 7. The mixed bed ion-exchange resin was then filtered off and the solvent removed by distillation under reduced pressure to leave approximately 30 grams of 3-[(3-cholamidopropyl)dimethylammonio]-2-hydroxy-1-propanesulfonate (50% theory). This material was judged to be homogeneous by thin layer chromatography on Silica Gel G in a 95% methanol/5% ammonium hydroxide solvent system followed by iodine visualization.

Calculated analysis for: $C_{32}H_{58}N_2SO_8 \cdot 1H_2O$ was: C, 59.22%; H, 9.32%; N, 4.31%, S, 4.94%. The experimental analysis found: C, 59.12%; H, 9.31%; N, 4.31%; S, 4.99%. Suggested trivial name CHAPSO.

In an evaluation of 3-[(3-cholamidopropyl)dimethylammonio]-2-hydroxy-1-propanesulfonate relative to CHAPS in the opiate receptor solubilization assay, solubilization and Sepharose 6B chromatography of active opiate receptors was performed as described by Simonds, et al, in *Proc. Nat. Acad. Sci. U.S.A.*, 77, 4623–4627 (1980). FIG. 2 demonstrates that 3[(3-cholamidopropyl)dimethylammonio]-2-hydroxy-1-propanesulfonate (CHAPSO) is about twice as effective as CHAPS at solubilizing active opiate receptors.

CHAPS itself may be prepared using as analogous alkylating agent sodium 1-chloro-propanesulfonate.

I claim:

1. A nondenaturing zwitterionic detergent for protein consisting of an effective amount of 3-[(3-cholamidopropyl)dimethylammonio]-1-propanesulfonate in a water carrier.

2. The process according to claim 1 of producing 3-[(3-cholamidopropyl)dimethylammonio]-1-propanesulfonate.

3. The compound 3-[(3-cholamidopropyl)dimethylammonio]-1-propanesulfonate.

4. The process according to claim 1 of producing 3-[(3-cholamidopropyl)dimethylammonio]-2-hydroxy-1-propanesulfonate.

5. The compound 3-[(3-cholamidopropyl)dimethylammonio]-2-hydroxy-1-propanesulfonate.

6. A process for producing a nondenaturing zwitterionic detergent for protein derived from the reaction of an acid selected from one member of a group of carboxylic acids consisting of cholic acid, deoxycholic acid, and dehydroabietic acid reacted with a polyethyleneamine selected from one member of the group consisting of

(1)

(2)

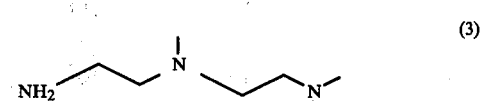

(3)

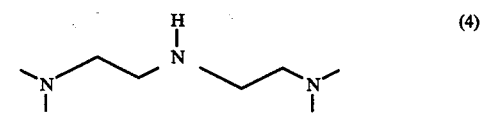

(4)

or reacted with a polypropyleneamine selected from one member of the group consisting of

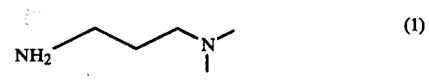

(1)

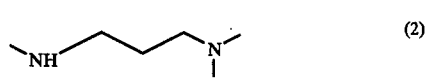

(2)

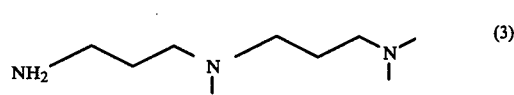

(3)

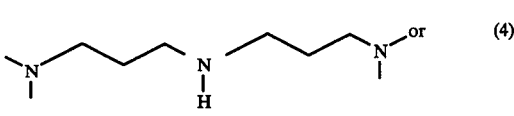

(4)

-continued

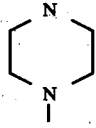

and reacted with an alkylating agent selected from one member of the group consisting of propanesultone, butanesultone, sodium 3-Cl,2-OH-propanesulfonate, sodium 2-Br-ethane sulfonate, and sodium chloroacetate wherein
(1) said carboxylic acid is reacted with an amine to form a triethylammonium salt in the solvent tetrahydrofuran;
(2) after the salt is completely dissolved, ethyl chloroformate is added and the flask is cooled to 0° C. and a precipitate forms which is triethylamine hydrochloride which is filtered away from the mixed anhydride;
(3) the product, mixed anhydride, reacts with a polyamine to form the polyamine derivative of a carboxylic acid amide as well as ethanol and carbon dioxide by products;

(4) the polyamine is reacted with an alkylating agent selected from one member of the group consisting of

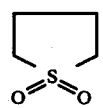 Propanesultone, (1)

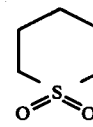 Butanesultone, (2)

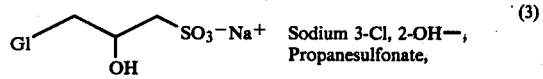 Sodium 3-Cl, 2-OH—, Propanesulfonate, (3)

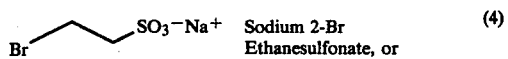 Sodium 2-Br Ethanesulfonate, or (4)

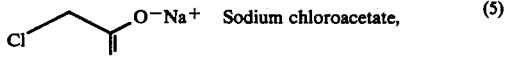 Sodium chloroacetate, (5)

to give the betaine.

* * * * *